United States Patent [19]

Darrow et al.

[11] Patent Number: 5,445,151
[45] Date of Patent: Aug. 29, 1995

[54] METHOD FOR BLOOD FLOW ACCELERATION AND VELOCITY MEASUREMENT USING MR CATHETERS

[75] Inventors: Robert D. Darrow, Scotia; Charles L. Dumoulin, Ballston Lake, both of N.Y.

[73] Assignee: General Electric Company, Schenectady, N.Y.

[21] Appl. No.: 264,281

[22] Filed: Jun. 23, 1994

[51] Int. Cl.⁶ ............................................. A61B 5/055
[52] U.S. Cl. .................................. 128/653.3; 324/306
[58] Field of Search ..................... 128/653.3; 324/306, 324/307

[56] References Cited

U.S. PATENT DOCUMENTS 3,191,119 6/1965 Singer .............................. 128/653.3
4,782,295 11/1988 Lew ................................. 128/653.3

Primary Examiner—Ruth S. Smith
Attorney, Agent, or Firm—Lawrence P. Zale; Marvin Snyder

[57] ABSTRACT

A method of magnetic resonance (MR) fluid flow measurement within a subject employs an invasive device with an RF transmit/receive coil and an RF transmit coil spaced a known distance apart. The subject is positioned in a static magnetic field. The invasive device is positioned in a vessel of a subject in which fluid flow is desired to be determined. A regular pattern of RF transmission pulses are radiated through the RF transmit/receive coil causing it to cause a steady-state MR response signal. Intermittently a second RF signal is transmitted from the RF coil positioned upstream which causes a change in the steady-state MR response signal sensed by the downstream transmit/receive coil. This is detected a short delay time later at the RF receive coil. The time delay and the distance between the RF coils leads directly to a fluid velocity. By exchanging the position of the RF transmit and transmit/receive coils, retrograde velocity may be measured. In another embodiment, more RF coils are employed. The changed MR response signal may be sensed at a number of locations at different times, leading to a measured change in velocity, or acceleration of the fluid.

6 Claims, 3 Drawing Sheets

METHOD FOR BLOOD FLOW ACCELERATION AND VELOCITY MEASUREMENT USING MR CATHETERS

CROSS REFERENCES TO RELATED APPLICATIONS

This application is related to U.S. patent applications Ser. No. 08/264,282, filed Jun. 23, 1994, "Magnetic Resonance (MR) Angiography Using a Faraday Catheter" by C. Dumoulin, S. Souza; (Ser. No. 08/264,283, filed, Jun. 23, 1994, "Magnetic Resonance (MR) Angiography in A Low-Field Imaging Magnet" by C. Dumoulin, R. Darrow; Ser. No. 08/175,448, filed Dec. 30, 1993, "Method For The Simultaneous Detection Of Acceleration and Velocity Distribution In Moving Fluids" by C. Dumoulin, all assigned to the present assignee, and all incorporated by reference.

BACKGROUND OF THE INVENTION

1. Field of the Invention

The present invention relates to the field of magnetic resonance imaging and more specifically to measurement of fluid flow with magnetic resonance.

2. Description of Related Art

Components of fluid motion, such as velocity and acceleration are important parameters to measure in many systems. These parameters are useful in determination of development of vascular diseases such as arteriosclerotic disease.

A traditional fluid flow analysis method, known as ink streamlining, requires introducing a contrast agent into a flowing fluid and observing the motion of the contrast agent.

Another method of measuring motion of materials employs laser Doppler technique. This requires a laser beam to be reflected from particles suspended in the material which is to be measured, and determining the displacement of each particle over a short interval thereby indicating the velocity of the material at the chosen location. Neither ink streamlining or laser Doppler methods are suitable for the detection of velocity within blood vessels.

An alternative method for the measurement of velocity in moving fluids within a vessel relies on Doppler shifts in reflected ultrasound signals. With this method, an ultrasound probe is placed near the vessel. Ultrasonic waves are transmitted into the vessel and reflected by the fluid. As the fluid moves, the frequency of the reflected ultrasonic waves is changed. For fluid moving towards the ultrasound probe, the reflected waves have a higher frequency, while reflected waves from fluid moving away from the probe have a lower frequency.

Ultrasonic measurement methods, however, are limited by the ability of the system to measure only the component of velocity directly to, or away from, the probe; and are limited by the need for the vessel to be surrounded by tissue which is transparent to ultrasonic energy.

A number of methods for the detection and measurement of fluid motion with magnetic resonance have been previously disclosed. These methods employ motion sensitive MR pulse sequences to identify the moving fluids.

There is a need for a simple method of determining components of fluid motion employing magnetic resonance.

SUMMARY OF THE INVENTION

An invasive device employs several small radio-frequency (RF) coils near its end. A subject is placed in a magnetic field and the invasive device is introduced into the subject. A downstream RF coil in the invasive device generates a series of RF pulses transmitted into the vicinity of the coil which induce a resonant MR response signal from selected nuclear spins within the subject. The RF coils sense the MR response signal produced from the subject. Since the RF coil is small, its region of sensitivity is limited. Consequently, only nuclear spins in the immediate vicinity of the RF coil are detected. This is repeated to produce a steady state MR response signal to be produced. Intermittently, an upstream RF coil produces an RF transmission. The MR response signal is monitored. The time is measured for a change in the steady-state MR response signal to be detected by the RF coils. Knowing beforehand the spacing between the RF coils, the fluid flow velocity can be computed. A receiver system receives the detected MR response signal and calculates the fluid flow velocity. If the transmission signals of the upstream and downstream RF coils are reversed, retrograde velocity is measured. In still another embodiment, several RF coils are used to determine velocity at several different points, thereby allowing change in velocity, or acceleration, to be determined.

OBJECTS OF THE INVENTION

It is an object of the present invention to provide a method for in-vivo measurement of fluid flow velocity within a subject.

It is an object of the present invention to provide a method for in-vivo measurement of fluid flow acceleration within a subject.

It is an object of the present invention to provide a method for in-vivo measurement of fluid flow retrograde velocity within a subject.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

In the present embodiment of the invention, a subject is placed within a static magnetic field, such as that of a magnetic resonance imaging system.

Figure 1:
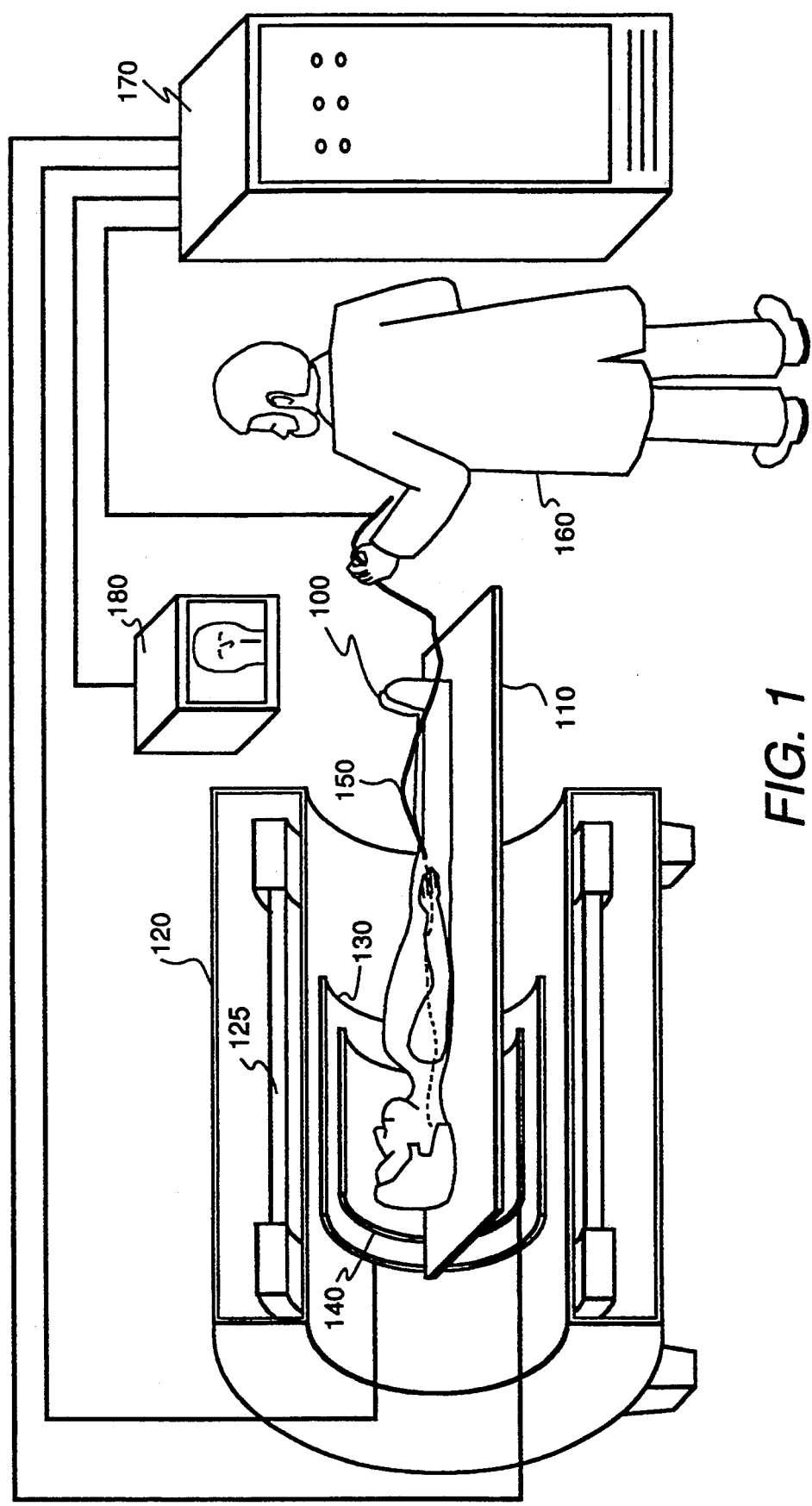
FIG. 1 is a perspective view of one embodiment of the present invention in operation tracking the location of a device in a subject.

In FIG. 1, a subject 100 on a support table 110 is placed in a homogeneous magnetic field generated by a magnet 125 in magnet housing 120, causing unpaired spinning nuclei, "spins" to resonate causing a net Longitudinal magnetization, $M_L$. Magnet 125 and magnet housing 120 in this embodiment have cylindrical symmetry and are shown sectioned in half to reveal the position of subject 100.

Subject 100 is surrounded by a set of cylindrical magnetic field gradient coils 130 which create magnetic field gradients of predetermined strength at predetermined times. Gradient coils 130 generate pulsed magnetic field gradients in three mutually orthogonal directions. The MR response signals received at RF coil 140 are passed to MR imaging electronics, shown here as cabinet 170 to perform image reconstruction as commonly known in the art, and then display the MR angiographic image on a display 180.

Figure 2:
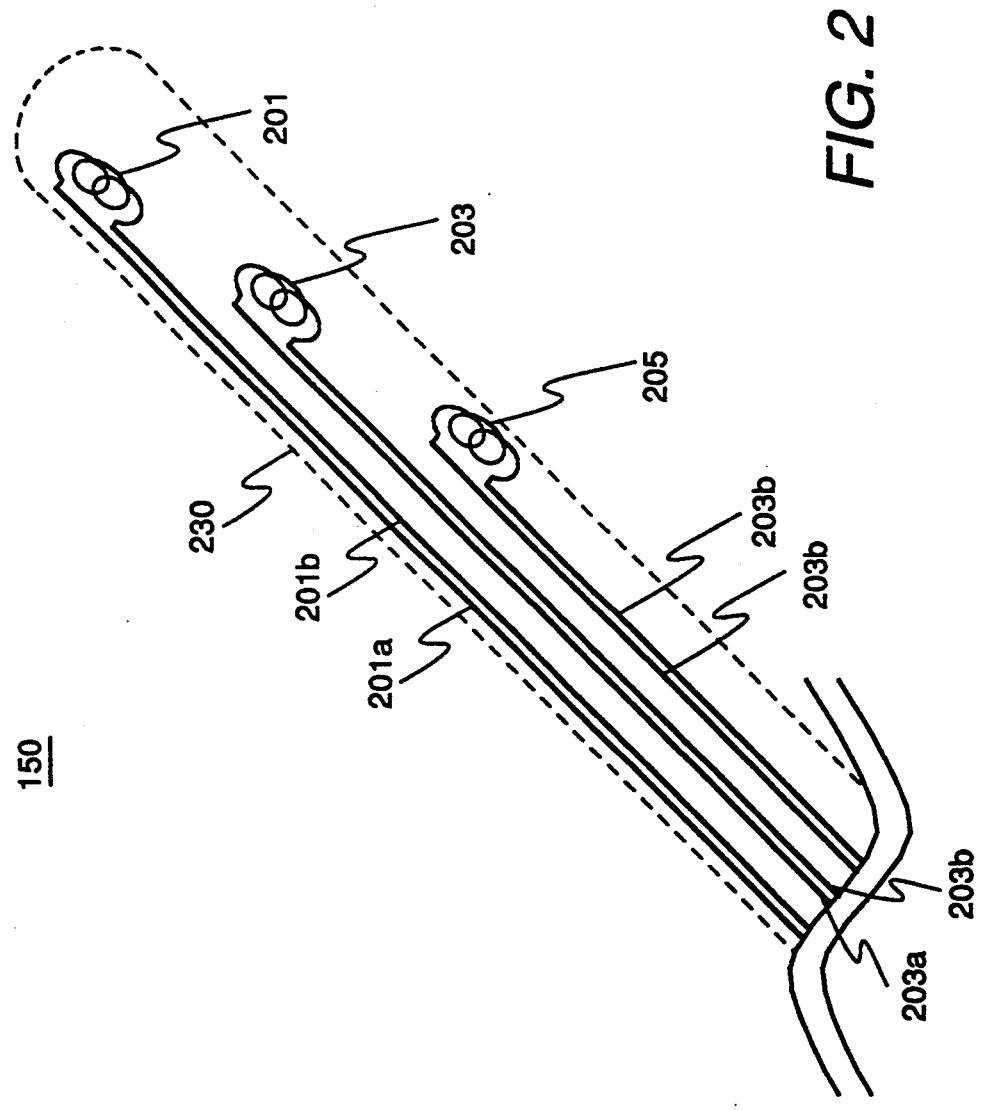
FIG. 2 is a schematic illustration showing a plurality of RF coils incorporated into an invasive device intended to be inserted into the body of a subject.

An embodiment of device 150 is shown in greater detail in FIG. 2. A plurality of small RF coils 201, 203, 205 are electrically coupled to the MR system via conductors 201a, 201b; 203a, 203b; 205a, 205b, respectively. In the preferred embodiment of this invention, conductors form a co-axial pair. The conductors and RF coils are encased in an outer shell 230 of device 150.

Invasive device 150 is inserted into subject 100 by an operator 160, and may be as a guide wire, a catheter, an endoscope, a laparoscope, a biopsy needle or similar device. The RF coils are capable of radiating RF energy into subject 100 of a frequency and amplitude to cause nutation of the "spins" of subject 100 near invasive device 150. Since RF coils are small, the transmit region and region of sensitivity are also small. Consequently, the transmitted signals affect spins in the immediate vicinity of RF coils 201,203,205; and the detected MR response signals which arise from the immediate vicinity of RF coil 201, 203, 205.

Device 150, shown as a catheter, is inserted, into a vessel of subject 100 at a location in which components of motion are desired to be measured and is positioned such that the RF coils are positioned upstream, and downstream with reference to each other, according to the normal direction of fluid flow.

In a first embodiment, the invasive device is positioned in a vessel with the fluid flowing by the end of invasive device 150 with coil 201, past coils 203 and 205. RF coil 201 is therefore upstream with respect to RF coils 203, which is upstream with respect to RF coil 205. RF coil 203 repeatedly radiates RF energy of a selected duration and intensity into subject 100 at the predetermined frequency at predetermined times and with sufficient power that nutates nuclear magnetic spins of subject 100, according to pulse sequence "rf1" of FIG. 3. Each application of RF energy forms a sampling RF pulse. The nutation of the spins causes a net transverse magnetization, $M_T$, of a population of spins which resonates at the Larmor frequency. The Larmor frequency for each spin is directly proportional to the strength of the magnetic field experienced by the spin. After repeated transmissions of sampling RF pulses from coil 203, a steady-state MR response signal is reached which may be sensed by a detection means attached to RF coil 203. Intermittently, RF coil 201 transmits RF energy according to pulse sequence "rf2" of FIG. 3, which creates a change in the longitudinal magnetization of the flowing fluid. Each application of RF energy to RF coil 201 forms a perturbation RF pulse. This change, or perturbation, in the preferred embodiment, leads to saturation of the nuclear spins, causing the "spins" to produce no MR response signal for a short time. This changes the steady state MR response signal sensed by RF coil 203. The time delay between when RF coil 203 transmits and the time in which the MR response signal changes at RF coil 203, coupled with known distances between the RF coils, results in a fluid flow velocity.

Note that the RF pulses applied to RF coil 201, 203 and 205 are independent of one another and can be applied with any desired timing. Note also that a more rapid application of the RF pulses of rf1 will permit a more accurate detection of velocity.

By adding more RF coils, the change in the MR response signal may be monitored at several different locations, thereby resulting in different velocity measurements over different positions. This may be used to determine fluid acceleration.

Figure 3:
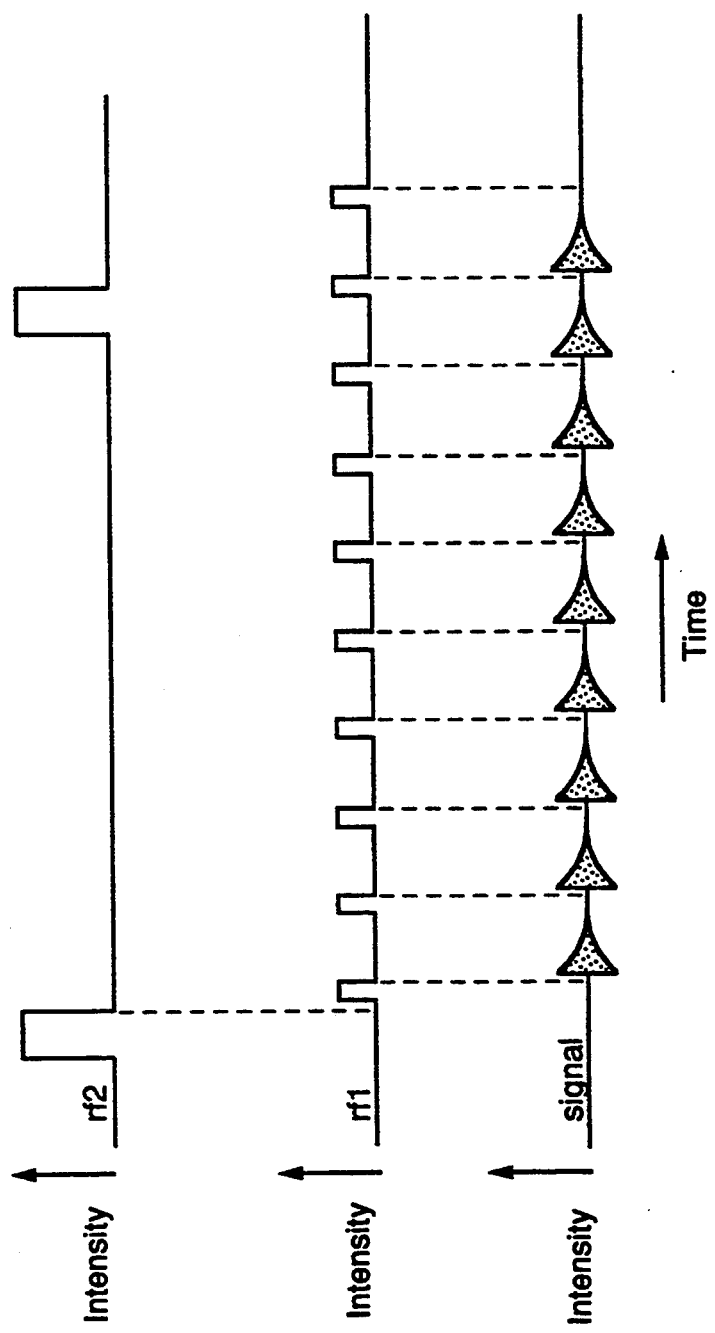
FIG. 3 is a timing diagram showing the relationships between RF pulses to an upstream RF coil, and RF pulses of a downstream RF coil on the catheter.

In another alternative embodiment, RF coil 205 transmits the intermittent "rf2" signal from FIG. 3; and RF coil 201 receives the MR response signal. This embodiment will measure fluid flow in a reverse direction, or retrograde velocity.

Similarly, by reversing the transmit and receive coils, retrograde acceleration may also be detected.

The present invention has several applications in medical diagnosis. For example, it may be used to detect stenosis.

All RF transmissions are non-spatially selective, that is they are transmitted in the absence of magnetic field gradients used to localize MR response signals and perform MR imaging. This invention therefore may be implemented without magnetic field gradient coils. It may also be implemented on a conventional MR Imaging system with the magnetic field gradient coils being inactive when the fluid flow velocity is being calculated.

While several presently preferred embodiments of the novel invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) fluid flow measurement system for measuring the flow of a fluid in a vessel of a subject comprising:
   a) means for applying a substantially homogeneous magnetic field over said subject;
   b) an invasive device for insertion into said subject;
   c) an RF transmit coil means attached to the invasive device at a first location, for transmitting intermittent perturbation RF pulses into said subject;
   d) an RF transmit/receive coil means, attached to the invasive device at a second location being a predetermined distance from the location of the RF transmit coil means, for transmitting sampling RF pulses into said subject and for receiving an MR response signal from said subject;
   e) a transmitter means, coupled to the RF transmit and RF transmit/receive coil means, for providing RF energy of a selected duration, amplitude and frequency to the RF transmit and RF transmit/receive coil means thereby causing nutation of a selected ensemble of spins in said subject when activated;
   f) a detection means attached to the RF transmit/receive coil means for detecting an MR response signal from the RF transmit/receive coil means when activated and for determining when a change has occurred in the received MR response signal;

g) a controller means coupled to the means for applying a substantially homogeneous magnetic field, transmitter means and the detection means, for activating the transmitter means at regularly spaced intervals causing the transmitter means to transmit a plurality of regularly spaced RF sampling pulses, and for intermittently activating the transmitter means causing the transmitter means to intermittently transmit perturbation pulses, and for activating the detection means causing the detection means to detect changes in the MR response signal; and h) a calculation means coupled to the transmitter means and the detection means for determining the time delay between transmission of an RF perturbation pulse and the change in a corresponding MR response signal and for calculating a first fluid flow velocity from this time delay and the predetermined distance.

2. The MR fluid flow measurement system of claim 1 further including:

a second RF transmit/receive coil means attached to the invasive device for exciting and receiving a second MR response signal; and the detection means measuring a second delay from the second MR response signal and providing this second delay to the calculation device for determining a second fluid flow velocity.

3. The MR fluid flow measurement system of claim 1 wherein the RF transmit coil means of the invasive device is positioned downstream in relation to an overall fluid flow direction of a vessel desired to be measured, with respect to the RF transmit/receive coil means in the invasive device, thereby measuring flow in a retrograde direction.

4. A method for measuring the flow of a fluid in a vessel of a subject comprising the steps of:

a) applying a substantially homogeneous magnetic field over said subject;

b) inserting an invasive device into said subject having an RF transmit coil, and an RF transmit/receive coil a known distance apart;

c) repeatedly transmitting RF energy of a selected duration, amplitude and frequency from the RF transmit/receive coil to cause nutation of a selected ensemble of spins in said subject;

d) detecting a steady-state MR response signal from the RF transmit/receive coil e) transmitting intermittent RF energy from the RF transmit coil so as to cause a change in the steady-state MR response signal detected by the RF transmit/receive coil;

f) determining a delay between when the intermittent RF energy signal was transmitted from the RF transmit coil to when a change in the steady-state MR response signal has occurred;

g) calculating a fluid flow velocity from the known distance between the RF coils and the measured delay.

5. The method of claim 4 wherein the step of inserting an invasive device comprises the step of positioning the invasive device with the transmit coil downstream, and the step of calculating a fluid flow velocity comprises the step of calculating retrograde fluid flow velocity.

6. The method of claim 4 further including the steps, after the step of determining a delay, the step of determining a second delay between when the intermittent RF energy signal was transmitted to when a change in the received MR response signal has occurred at a second RF receive coil; and after the step of calculating a fluid flow velocity the steps of calculating a second fluid flow velocity from the second delay and calculating an acceleration from the calculated fluid flow velocities.

* * * * *